(12) United States Patent
Feng et al.

(10) Patent No.: US 8,552,058 B2
(45) Date of Patent: Oct. 8, 2013

(54) APPLICATION OF L-N-BUTYLPHTHALIDE IN PREVENTING AND TREATING DEMENTIA

(75) Inventors: Yipu Feng, Beijing (CN); Xiaoliang Wang, Beijing (CN); Rongduan Wang, Shijiazhuang (CN); Ying Peng, Beijing (CN); Liying Yang, Shijiazhuang (CN); Jinghua Yang, Beijing (CN); Jingguo Sun, Shijiazhuang (CN); Zhankun Yang, Shijiazhuang (CN)

(73) Assignee: CSPC Zhongqi Pharmaceutical Technology (Shijazhuang) Co., Ltd., Shijiazhuang, Hebei (CN)

( * ) Notice: Subject to any disclaimer, the term of this patent is extended or adjusted under 35 U.S.C. 154(b) by 711 days.

(21) Appl. No.: 11/629,964

(22) PCT Filed: Jun. 18, 2004

(86) PCT No.: PCT/CN2004/000652
§ 371 (c)(1),
(2), (4) Date: Dec. 18, 2006

(87) PCT Pub. No.: WO2005/002568
PCT Pub. Date: Jan. 13, 2005

(65) Prior Publication Data
US 2007/0265336 A1 Nov. 15, 2007

(51) Int. Cl.
*A01N 43/08* (2006.01)
*A61K 31/34* (2006.01)
*C07D 307/00* (2006.01)

(52) U.S. Cl.
USPC .................. 514/470; 514/469; 549/466

(58) Field of Classification Search
USPC .................. 514/470, 469; 549/466
See application file for complete search history.

(56) References Cited

U.S. PATENT DOCUMENTS 6,447,814 B1 * 9/2002 Lee et al. ............ 424/725

FOREIGN PATENT DOCUMENTS

| CN | 1100097 A | | 3/1995 |
|---|---|---|---|
| CN | 1283621 A | | 2/2001 |
| CN | 1 369 290 A | | 9/2002 |
| CN | 1375288 A | | 10/2002 |
| CN | 1 446 565 A | | 10/2003 |
| CN | 1446565 A | * | 10/2003 |
| CN | 1394880 A | | 2/2006 |
| EP | 1 679 070 A1 | | 7/2006 |
| JP | 64-50817 A | | 2/1989 |
| JP | 4-210634 A | | 7/1992 |
| JP | 5-247022 A | | 9/1993 |
| WO | WO 0200638 | * | 3/2002 |
| WO | 2004/018444 A1 | | 3/2004 |
| WO | 2005/034936 A1 | | 4/2005 |

OTHER PUBLICATIONS

Yu et al. (Acta Pharmacologica Sinica, Sep. 9, 1988, (5), 385-388).*
Qing et al. (J Acta Pharmacol Sin Aug. 24, 2003(8): 796-804).*
Alzheimer's and Dementia Document (p. 1-4).*
Xu et al. (Acta Pharmaceutica Sinica 1999, 34(3) 172-175).*
Zhaozhong et al. (Chinese Med J 2000, 115, 7, 613-616).*
Williams et al (Foye's Principles of Medicinal Chemistry, 5th Edition, p. 50, 2002).*
Kwan et al. (Archives of Neurology, 1999, 56, 809-814).*
Moyler (Flavour and Fragrance Journal, vol. 8, 235-247, 1993).*
Chong ZZ et al., "Effect of di-n-butylphthalide on the activity of the choline acetyltransferase in ischemic brain and cultured neurons subjected to hypoglycemia/hypoxia", Clin Pharm J, vol. 34, No. 8, pp. 519-522 dated Aug. 1999.
Dong Gao-xiang et al., "Effect of NBP on ATPase and Anti-oxidant Enzymes Activities and Lipid Peroxidation in Transient Focal Cerebral Ischemic Rats", ACTA Academiae Medicinae Sinicae, vol. 24, No. 1 dated Feb. 2002.
Bjeldanes, L.F. et al., "Phthalide Components of Celery Essential Oil" *Journal of Organic Chemistry* (1977) pp. 2333-2335, vol. 42(13).
Bartschat, D. et al., "Stereoisomeric Flavor Compounds. 79. Simultaneous Enantioselective Analysis of 3-Butylphthalide and 3-Butylhexahydrophthalide Stereoisomers in Celery, Celeriac, and Fennel" *Journal of Agricultural and Food Chemistry* (1997) pp. 4554-4557, vol. 45(12).
Bartschat, D. et al., "Stereoisomeric Flavour Compounds LXXIII: 3-Butylphthalide: Chirospecific Analysis, Structure and Properties of the Enantiomers" *Phytochemical Analysis* (1996) pp. 131-135, vol. 7(3).
MacLeod, A.J. et al., "Volatile Aroma Constituents of Celery" *Phytochemistry* (1988) pp. 373-375, vol. 27(2).
Zhang, J.T. et al., "New Drugs Derived from Medicinal Plants" *Database Medline, US National Library of Medicine* (2002) pp. 137-150, vol. 57(2).
Supplementary European Search Report dated Jan. 13, 2010.
He J. et al., "Development of treatment in Senile dementia with Chinese medicine", Gansu Journal of Traditional Chinese Medication 1:43-47 (1999) together with English language abstract.

(Continued)

*Primary Examiner* — Sreeni Padmanabhan
*Assistant Examiner* — Uma Ramachandran
(74) *Attorney, Agent, or Firm* — Scully, Scott, Murphy & Presser, P.C.

(57) ABSTRACT

The invention discloses the application of l-n-butylphthalide as formula (I) in preparing a medicine for preventing and treating dementia, in special Alzheimer's disease and vascular dementia.

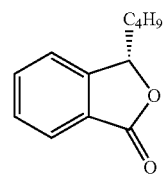

(I)

6 Claims, 6 Drawing Sheets (56) References Cited

OTHER PUBLICATIONS

Ma Q. et al., "Mechanism of treatment of Alzheimer's disease with active ingredients of traditional Chinese medicine", Chinese Traditional Herb Drugs 4:243-243 (1997) together with English language abstract.

Xiao S. et al., "Present situation and prospect of Chinese medicine treatment of vascular dementia", Journal of Traditional Chinese Medicinal literature 1:42-44 (2001) together with English language abstract.

Yamagishi T. et al., "Constituents of Cnidium officinale Makino. Structure of Senkyunolide and Gas Chromatography—Mass Spectrometory of the Related Phthalides" 97:237-243 (1977) together with English language abstract.

Yu S. et al., "Serial development of Anticonvulsant action of celery" Pharmacology and Clinics of Chinese Materia Medica 00:94 (1985) together with English language abstract.

* cited by examiner

APPLICATION OF L-N-BUTYLPHTHALIDE IN PREVENTING AND TREATING DEMENTIA

FIELD OF THE INVENTION

The present invention relates to the use of L-n-butylphthalide and a composition comprising L-n-butylphthalide for treating dementia.

BACKGROUND OF THE INVENTION

Senile dementia, also known as Alzheimer's disease (AD), is a progressive and degenerative neuropathy with clinical and pathological features. Its clinical manifestations mainly are memory (particularly immediate memory) loss, low cognition, retarded thinking, dysfunctional stereogenosis, among others. And its pathological manifestations are the extracellular deposition of amyloid-β (Aβ) which aggregate with other molecules, neurons and non-neural cells to form senile plaques and intracellular neurofibrillary tangles (NFT). In China, the morbidity of AD is in the range of 0.2%-5.98% and increases with the age. It mainly occurs in people above 60-year-old. More than 3.6 millions of people are estimated to be suffering from AD now in China. In a dementia survey in Beijing, it is discovered that the morbidity of vascular dementia is higher than that of AD (Mingyuan Zhang et al., the morbidities of dementia and Alzheimer's Disease. Chinese Journal of Psychiatry 1998; 31(4):195-196). As China is becoming an aged society, the number of dementia patients increases over time. In addition, the morbidity of cerebrovascular diseases is high in old people. The incidence of dementia after apoplexia is estimated to be approximately 9-30.8%. Chronic poor blood supply to brain is another important cause for vascular dementia. In summary, dementia is harmful to patients and loads huge burden to families and the society. Accordingly, it is of great importance to search for an effective medicine to delay and control the development of AD and VD.

Alzheimer's Disease (AD) is the most common cause for the progressive decrease of cognition in old people. Pathological change of AD is mainly presented as the formation of senile plaque with the core of deposited amyloid-β and intracellular neurofibrillary tangles (NFT). Researches have shown that the cholinergic system in the brain was associated with learning and memory functions of human. Cerebral ACh level in AD patients decreases and the activity of choline acetyltransferase, which catalyses the synthesis of ACh, is reduced. The degree of the decrease is closely related with the cognition loss. Furthermore, Oxidative stress and inflammatory reaction are increasingly considered being involved in the pathology of AD. Aβ is composed of 39-43 amino acids, and is the degradation product of amyloid-β precursor (APP). The extent of Aβ deposition is closely associated with neural damages and cognition defects. It is demonstrated in previous studies that continuous i.c.v. perfusion of Aβ (1-40) or Aβ (1-42) would induce damages to the learning and memory of rats (Nitts. et al., β-Amyloid protein-induced Alzheimer's disease animal model. Neurosci. Lett. 1994; 170:63-66), which suggested that memory damage by Aβ aggregation could mimic symptoms of AD patients. L-n-butylphthalide (L-NBP) was shown to have brain-protecting function, for example, the ability to significantly improve mitochondrial function, to improve cerebral microcirculation and energy metabolism, to inhibit neuronal apoptosis, to protect from oxidative damage, to inhibit inflammatory response, to inhibit thrombosis, to reduce intracellular calcium, and to inhibit glutamate release. As such, continuous i.c.v. perfusion of Aβ (1-40) can be used as a model. Morris' water maze and biochemical assays are used to detect the effects of test compounds on short-term memory, stereognosis and oxidative damage in animals.

Vascular dementia (VD) is derived from brain dysfunction induced by cerebrovascular diseases, usually with complications such as multiple infarction of large cerebral arteries, lacunal infarction and brain hypoperfusion. The reduction of cerebral blood flow is associated with the severity of dementia (Roman et al., Vascular dementia: diagnostic criteria for research studies. Neurology 1993; 43:250-260). Chronic progressive poor blood supply to brain causes reduced availability of oxygen, glucose and other essential metabolites, resulting in oxidative damages, impairing mitochondrial functions and biosynthesis in neuronal cells, impeding synaptic transmission, and eventually causing neuropathological changes, i.e. neurodegenerative changes (Beal et al. Do defects in mitochondrial metabolism underlie the pathology of neurodegenerative disease. Trends Neurosci. 1993; 16:125-131). VD patients mainly present progressive loss of short-term memory and stereognosis as well as cognition dysfunction. The occurrence and development of vascular dementia is closely associated with signal transduction of cholinergic neural system, and is also associated with oxidative damage of neural cells. Substantia alba beneath the cortex is pathologically sparse in VD patients. It was shown in extensive investigation that ACh was considered as an important neural transmitter in learning and memory. The cholinergic pathway in AD patients is functionally impaired, with the representation of reduced level of neural transmitter ACh, which is one of the important reasons for the impaired memory and cognition defect (Toghi et al., Cerebrospinal fluid acetylcholine and choline in vascular dementia of Binswanger and multiple small infarct types as compared with Alzheimer-type dementia. J. Neural Transm. 1996; 103:1211-1220). The test compounds can improve ChAT activity, suggesting its ability to increase cholinergic ACh level, which contributes to improve memory function.

During the recent ten years, Morris' water maze has been employed in many studies to test short-term memory and stereotaxic memory of rats, which can sensitively reflect the damages and functional changes of an animal's central neural system (Richard Morris. Developments of a water-maze procedure for studying spatial learning in the rat. J. Neurosci. Methods 1984; 11:47-60), and the effect of test medicines can be observed on this model. Since the main symptom of dementia patients is cognition defect, in particular progressive damage of short-term memory and stereognosis, this is an ideal model for investigating the therapeutic effects of test medicines on presenile dementia (AD) and VD. Continuous hypoperfusion in the rat model of bilateral common carotid artery occlusion may be employed to simulate vascular dementia induced by clinical poor blood supply, and thus can be used to reflect the therapeutic effects of the test medicines on dementia (Ni. J. W. et al. Neuronal damage and decrease of central acetylcholine level following permanent occlusion bilateral common carotid arteries in rats. Brain Res. 1995; 673:290-296).

In 1988, Shuren Yu reported that 3-n-butylphthalide (Ag-1), as a synthetic racemic 3-n-butylphthalide, could be used to improve the impaired learning and memory induced by coriamyrtin in rats and protect hippocampal cells (Shuren Yu, et al. Effect of butylphthalide to improve learning and memory. Chinese Journal of Pharmacology. 1988; 9(5):385-388). Later, celery extract was reported to improve learning and memory in mice of middle and old age (Jing Li, et al. Effect of celery extract on learning and memory in mice of middle and old age. Chinese Traditional and Herbal Drugs 1996; 27(2):104-105; Luosheng Liu, et al. Study on quality standards of ANQINGYIZHI capsule. Journal of Shandong Medical University 2001; 39(6):562-564). But it is not yet reported that an optical stereoisomer, L-n-butylphthalide (L-NBP), can be used to treat senile dementia.

SUMMARY OF THE INVENTION

To overcome the disadvantages in the prior art, the present invention provides use of L-n-butylphthalide (L-NBP) represented in formula (I) as an anti-dementia drug.

(I)

L-n-butylphthalide used in the present invention may be obtained by firstly chemically synthesizing racemic n-butylphthalide, and then chemically resolving to produce a levorotary optical isomer of n-butylphthalide. After spectroscopic analysis such as nuclear magnetics, mass spectrometry, and infrared spectrometry, especially gas chromatography in HP 5890 equipped with chiral gas chromatographic column (Chiraldex G-TA), it was confirmed that the product obtained was a separate optical stereoisomer in terms of optical purity and chemical purity and the product was levorotary n-butylphthalide, (specific optical activity>−66.490, optical purity>98%, and chemical purity>98%). The procedure for resolution can be carried out as a taught in Chinese Patent Application titled "A method for preparing the optical active 3-n-butylphthalide" with Application No. 99109673.8 and Publication No. CN1283621. The product thus obtained has a chemical formula identical to that of n-butylphthalide contained in edible celery and seeds thereof.

In the present invention, short-term memory and stereognosis of animals was tested using an internationally accepted method of Morris' water maze.

In the present invention, a continuous hypoperfusion model was established by permanent occlusion of bilateral common carotid artery (2-VO), then the effects of L-NBP on short-term memory and stereognosis of animals were determined using the method of Morris' water maze, and the effects of L-NBP on certain aspects of oxidative damages and on the cholinergic neural system were determined by biochemical assays. Given that brain hypoperfusion induces behavioral changes accompanied by the activation of glial cells and sparse substantia alba, pathological and immunohistochemical methods were employed in the present invention to investigate the effects of the medicament with Glial Fibrillary Acidic Protein (GFAP) and K-B staining (indicating pathological changes of neural myelin sheath) as the indicators.

It was shown in the experiment that L-n-butylphthalide of the present invention could significantly improve the function of short-term memory and stereognosis in rats with poor blood supply to brain. The learning and remaining test in the water maze method is often employed to evaluate spatial memory in hypoperfused rats. Results in the water maze experiment showed that no significant difference existed among latencies of all groups in day 1, suggesting that all animals were not familiar with the procedure of this experiment on day 1. After 5 days of training, the search strategies of rats in the sham surgery group changed from peripheral and random to purposive and linear, and the latencies reduced significantly (12.6±3.34 sec), suggesting that the animals had achieved a certain degree of memory and spatial orientation after training. Comparatively, the search strategies of the rats in the solvent control group had no significant change and were still peripheral and random, and the latencies (47.6±5.88 sec) had no significant reduction. Significant difference existed between these two groups (p<0.01). The search strategies of the 10 mg/kg L-NBP group changed from peripheral and random to purposive and linear, and the latencies (26.85±5.98 sec) reduced obviously, which were significantly different from those of the solvent control group (p<0.001, two-factor analysis of variance) but had no significant difference as compared with those of the sham surgery group. It suggested that this dosage group could significantly improve memory and spatial orientation. Other drugs such as 10 mg/kg DL-NBP, 30 mg/kg DL-NBP, and 30 mg/kg D-NBP had no significant effect of improvement.

When the 5 days' learning and training period ended, a platform exploration test was performed. A safety island was removed in order to determine whether the rats had kept a relative position of the safety island in memory. Except for the solvent control group, all rats in the other groups had a detention time in the target quadrant of above 25%, suggesting that they had kept a relative position of the safety island in memory. The detention time of the sham surgery group was 17.73±1.19 seconds, while that of the solvent control group (14.40±0.73 sec) was significantly reduced. As determined by one-factor statistic analysis of variance, significant difference existed between both groups (p<0.05). The detention time of 10 mg/kg L-NBP group at the quadrant where the platform was located (17.62±1.27 sec) was evidently extended as compared with that of the solvent control group. Significant difference existed between the two groups (p<0.05). Both of DL-NBP groups (10 mg/kg and 30 mg/kg) showed no effect. It was determined that no difference existed among the swimming speeds of the groups, thus eliminating the variation derived from animal mobilities. The results above indicated that only L-n-butylphthalide could significantly improve short-term memory and spatial orientation in rats with poor blood supply to brain, but racemic (DL-) and D-n-butylphthalide could not.

SOD is one of the important anti-oxidative enzymes. In the normal control group of rats, the activity of SOD was 100.07±3.64 (NU/mg protein) in the cortex tissues, and 57.90±7.41 (U/mg protein) in the hippocampal tissues. After permanent ligation of bilateral common carotid arteries, the SOD activity in hippocampus significantly increased as compared with that of the control group (p<0.05), which could be a compensatory response. After a treatment with L-NBP (10 mg/kg), the SOD activity evidently returned to the normal level (p<0.05). MDA is a marker of lipid peroxidation, and could indicate the level of lipid peroxidation in vivo and indirectly indicate the degree of cell damage. In this experiment, the MDA content in the cortex of the model group increased 19.9%, which was significantly different from that of the normal control group (p<0.001). After a treatment with L-NBP (10 mg/kg), the MDA content in the cortex significantly reduced 20.7% (p<0.001). After permanent ligation of bilateral common carotid arteries, the CHAT activity in the cortex significantly reduced 34.4% as compared with that of the normal control group (p<0.05), suggesting that hypoperfusion could induce damages to cholinergic neural functions.

Comparatively, after continuous administration of L-NBP (10 mg/kg) for 16 days, the ChAT activity in the cortex tissue could be improved 37.1% as compared with that of the model group, representing significant difference (p<0.05). From the results above, it can be concluded that 10 mg/kg L-NBP could significantly ameliorate disorders in short-term memory and spatial orientation of 2-VO animals, while neither racemic butylphthalide nor D-butylphthalide was effective to ameliorate disorders of memory. In the present invention, the administration began on the $10^{th}$ day after 2-VO (and until the $35^{th}$ day), in order to investigate the therapeutic effects of drugs on the degenerative changes of neurons induced by hypoperfusion and thus to eliminate the influence of the acute hypoperfusion ischemia phase.

Figure 1:
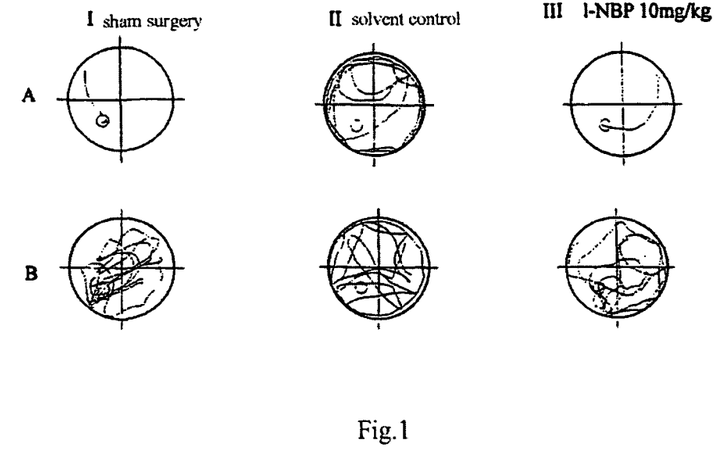
FIG. 1. Water maze experiments. 1A, search tracks of rats on the 5$^{th}$ day; 1B, search tracks of rats in platform exploration tests on the 5$^{th}$ day.
Figure 2:
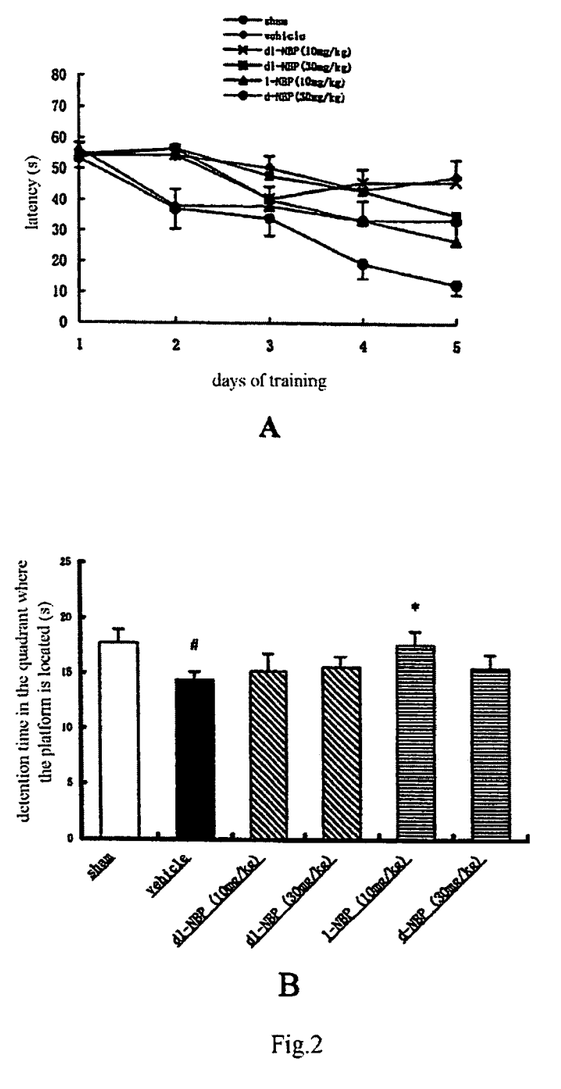
FIG. 2. Effects of oral L-NBP on impaired sterotaxic memory of rats in water maze experiments after permanent ligation of bilateral common carotid arteries.
Figure 3:
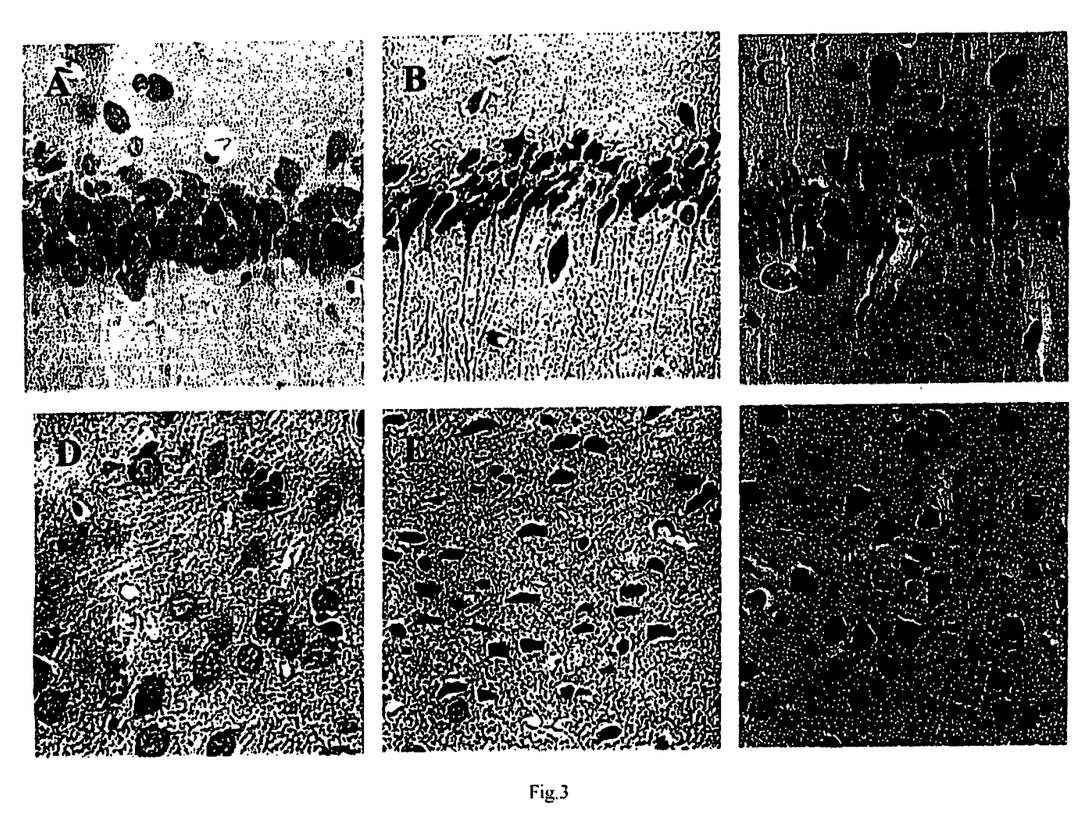
FIG. 3. Microscopic changes of H-E staining in hippocampal CA1 region (A, B, and C) and cortex (D, E, and F) 5 weeks after ligation of bilateral common carotid arteries in rats (40× magnification). Sham surgery group (A and D); solvent control group (B and E); L-NBP (10 mg/kg) treatment group (C and F) were included.
Figure 4:
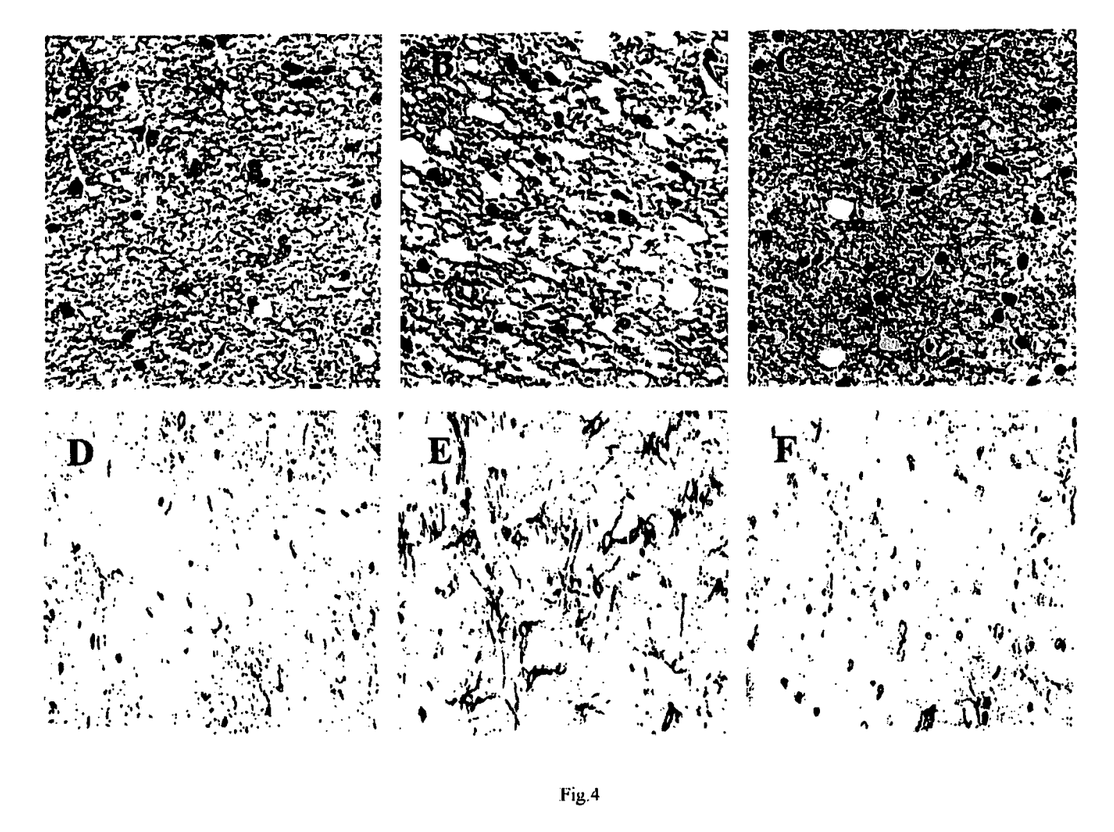
FIG. 4. Microscopic changes of K-B staining in optic tract (A, B, and C, 40× magnification) and GFAP immunohistochemical staining in caudate nucleus (D, E, and F, 20× magnification) 5 weeks after ligation of bilateral common carotid arteries in rats. Sham surgery group (A and D); solvent control group (B and E); L-NBP (10 mg/kg) treatment group (C and F).

Through pathological and immunohistochemical investigations, the present invention demonstrated that L-NBP had evident therapeutic effects on vascular dementia. After permanent ligation of bilateral common carotid arteries in the rats, the number of neurons was significantly reduced in the cortex and hippocampal CA1 regions in the model group, cells wrinkled and neurons were strongly stained. Comparatively, the neuronal damages induced by hypoperfusion could be significantly ameliorated by L-NBP (10 mg/kg) treatment. It was reported that bilateral common carotid artery ligation could induce the activation of glial cells in brain, accompanied with sparse substantia alba. Substantia alba is generally classified into 4 grades according to the severity of the sparsity: grade 0, normal; grade 1, misarrangement of nerve fibres; grade 2, evident formation of vacuola; grade 3, disappearance of fibres with myelin sheath. In our experiment, compared with the normal control group, optic tracts in the model group presented evidently sparse substantia alba and a number of vacuola appeared. Extended administration of L-NBP (10 mg/kg) could evidently ameliorate the condition, resulting in significant reduction of vacuola in optic tracts. It was shown in immunohistochemical experiments that GFAP-positive astrocytes were rarely detected in regions such as hippocampus, caudate nucleus, and corpus callosum in the normal group, but after bilateral ligation of common carotid arteries for 4 weeks, plenty of GFAP-positive astrocytes and microglial cell appeared. After treatment with L-NBP (10 mg/kg), the number of GFAP-positive astrocytes greatly reduced (see FIGS. 3, 4). In conclusion, L-NBP could improve ChAT activity, suggesting that L-NBP could increase the level of ACh in cholinergic neurons and thus could contribute to improve memory. In addition, L-NBP could significantly inhibit oxidative damages, suggesting that L-NBP could reduce the damages to neural cells. Cerebral hypoperfusion induced by 2-VO was characterized in sparse substantia alba, and the increased number of vacuola and glial cells (Narri. et al. Chronic cerebral hypoperfusion-induced neuropathological changes in rats. Jpn. J. Psychopharmacol. 1998; 18:181-188), while L-NBP could ameliorate all these pathological changes. The mechanism above presented the evidence that L-NBP could ameliorate memory disorder induced by 2-VO in rats. Based on the results above, L-NBP is evidently effective for therapeutic treatment of vascular dementia.

Figure 6:
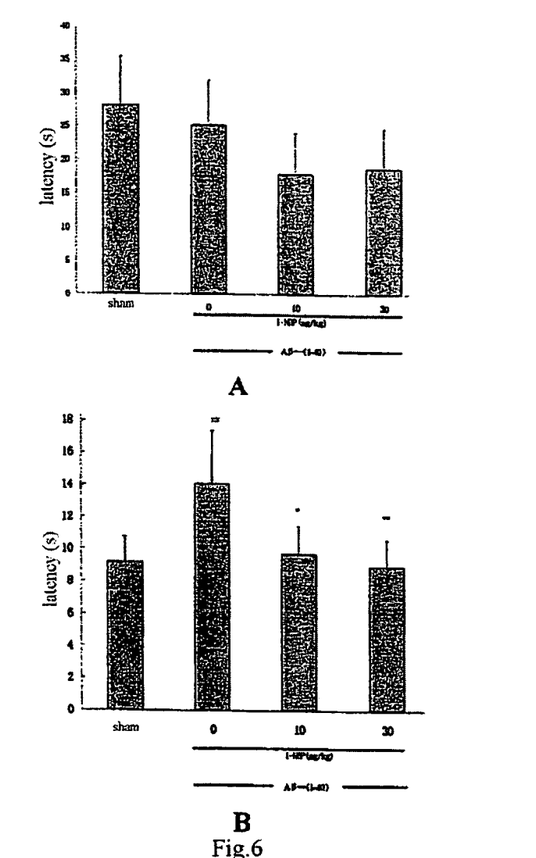

It was shown in the experimental results of the invention that disorders of memory and spatial orientation induced by amyloid-β (1-40) could be significantly ameliorated by L-n-butylphthalide of the present invention. The water maze experiment was performed after continuous perfusion of Aβ into rat intracerebroventricularly. On the first day of training, no significant difference existed between the latencies of the groups. After 5 days of training, the search strategies of rats in the sham surgery group changed from peripheral and random to purposive and linear, and the latencies reduced significantly (13.02±2.77 sec). Comparatively, the search strategies of rats in the model group had no obvious change and were still peripheral and random, and their latencies (30.18±4.81 sec) had no significant reduction. Significant difference existed between these two groups (p<0.01). After L-NBP treatment, the latencies of the rats in the water maze experiment significantly reduced. The search strategies of both of 10 mg/kg and 30 mg/kg L-NBP groups changed from peripheral and random to purposive and linear, and the latencies were 27.28±6.42 and 25.88±5.51 sec respectively, which were significantly different from those of the model group (p<0.05, two-factor analysis of variance), yet not significantly different from that of the sham surgery group. It suggested that the rats treated by L-NBP had been close to the normal level (see FIG. 4). In the working memory test, the latencies in the $1^{st}$ experiment and in the $2-5^{th}$ experiments could be seen in FIGS. 6A and 6B. While no significant difference existed between the latencies of the groups in the $1^{st}$ experiment, the latency of the sham surgery group was 9.15±0.91 sec and that of the model group was 14.05±1.88 sec in the subsequent 4 experiments. The latter was significantly extended, and significant difference existed between them (p<0.01). The L-NBP group can significantly improve the working memory ability in a dose-dependent way (p<0.01).

In addition, L-NBP could increase the activity of GSH-Px and reduce the level of MDA. GSH-Px is an important anti-oxidative enzyme. In our experiments, the activity of GSH-Px in the cortex tissues of the sham surgery group was 15.86±0.91 (U/mg protein); and the activity of GSH-Px in the hippocampal tissues was 16.19±1.19 (U/mg protein). After continuous perfusion of Aβ (1-40) in rats, the activities of GSH-Px in the cortex and the hippocampal tissues reduced respectively 29.5% and 42.4% as compared with that of the sham surgery group, showing significant differences (p<0.01 and p<0.001). After L-NBP treatment, the activity of GSH-Px in the 30 mg/kg L-NBP group increased significantly (p<0.01), while 10 mg/kg of L-NBP could also increase the activity of GSH-Px, but with no statistically significant difference. MDA is a marker of lipid peroxidation, indicating the degree of lipid peroxidation in vivo, and indirectly indicating the degree of cell damages. In the present experiment, after continuous perfusion of Aβ (1-40) in rats, cortical and hippocampal MDA contents increased 25.7% and 23.6% respectively, and were significantly different from those of the sham surgery group (p<0.05 and P<0.01). After L-NBP treatment, cortical and hippocampal MDA contents significantly reduced, being respectively 28.4% and 24.3% in the 10 mg/kg group (p<0.05 and p<0.01), and a little weaker in the 30 mg/kg group than in the 10 mg/kg group, yet still significantly different from those of the Aβ (1-40) model group (p<0.05).

It can be concluded from the present experiments that impaired memory induced by continuous perfusion of Aβ (1-40) in rats was a well-established model to investigate the therapeutic effects of medicines on AD. From the above results, it can be seen that L-NBP had evident effects on the model of vascular dementia resulting from poor blood supply induced by 2-VO, but also can significantly ameliorate impaired short-term memory and stereotaxic memory induced by continuous perfusion of Aβ (1-40) into lateral ventricle in rats. It suggested that L-NBP could significantly ameliorate impaired short-term memory and stereotaxic memory induced by various causes. Furthermore, L-NBP could prevent oxidative damages (increasing the activity of GSH-Px and reducing the content of MDA). Because of this activity together with its evident brain-protecting effect, L-NBP may be useful in therapeutically treating senile dementia.

In conclusion, in the present invention, short-term memory and stereotaxic memory of rats were evaluated using Morris' water maze and vascular dementia induced by clinical poor blood supply was simulated using continuously hypoperfused 2-VO model rats, so the present method can reflect the therapeutic effects of medicines on dementia. The results of the present invention demonstrated that 10 mg/kg L-NBP could significantly ameliorate impaired short-term memory and stereotaxic memory in 2-VO animals, while racemic butylphthalide or D-butylphthalide was uneffective to ameliorate impaired memory. ACh are considered as an important neural transmitter involved in learning and memory. The cholinergic pathways in AD patients are suppressed, as indicated by the reduced level of the neural transmitter ACh, which is one of the important reasons responsible for impaired memory and cognition damage. L-NBP could improve ChAT activity, demonstrating that L-NBP could increase ACh levels of cholinergic nerve to improve memory functions. L-NBP could significantly suppress oxidative damages, demonstrating that L-NBP could reduce damages to neural cells. Cerebral hypoperfusion induced by 2-VO is pathologically characterized in sparse substantia alba, vacuola and increased number of glial cells, all of which could be ameliorated by L-NBP. L-n-butylphthalide of formula (I) according to the present invention, therefore, could prevent and treat vascular dementia.

Continuous perfusion of Aβ (1-40) into lateral ventricle induced impaired learning and memory in rats, which simulates symptoms of patients with presenile dementia. Short-term memory and stereotaxic memory in rats were determined using Morris' water maze. L-NBP could significantly ameliorate both impaired short-term memory and stereotaxic memory, while neither D-NBP nor DL-NBP showed similar effects. GSH-Px is one of the important anti-oxidative enzymes; and MDA indicates the degree of lipid peroxidation in vivo, indirectly indicating the degree of damages to brain cells. L-NBP could improve GSH-Px activity and reduce MDA content, which suggested L-NBP could suppress oxidative damages and prevent brain damages. But neither D-NBP nor DL-NBP showed similar effects. L-n-butylphthalide of formula (I) according to the present invention, therefore, could prevent and treat presenile dementia. In summary, L-n-butylphthalide could prevent and treat senile dementia, while neither racemic butylphthalide nor D-n-butylphthalide showed similar effects.

The present invention also relates to a pharmaceutical composition comprising the compound of the present invention as active ingredient, and conventional pharmaceutically acceptable excipients or adjuvants. Generally, the pharmaceutical composition of the present invention comprises 0.1-95wt % of the compound of the present invention.

A pharmaceutical composition comprising the compound of the present invention may be prepared according to the methods well known in the art. For this purpose, the compound of the present invention may be combined with one or more pharmaceutically acceptable solid or liquid vehicles and/or adjuvants if desired, so as to be formulated into suitable administration forms or dosage forms for human use or veterinary use.

The compound of the present invention or the composition comprising the compound may be administered in unit dosage form, and the administration route may be gastrointestinal or parenteral, such as oral, intramuscular, subcutaneous, nasal, oral mucosal, transdermal, intraperitoneal, rectal, or the like.

The administration route of the compound of the present invention or the pharmaceutical composition comprising the compound may be via injection, including intravenous, intramuscular, subcutaneous, intracutaneous, and intra-acupointal injections, and the like.

The administration formulation may be liquid or solid. For example, the liquid formulation may be a solution, colloid, microparticulate, emulsion, or suspension. Other formulations may also be used, such as tablet, capsule, pill, aerosol, pellet, powder, solution, suspension, emulsion, granule, suppository, and lyophilized powder, and the like.

The compound of the present invention may be prepared as conventional formulations, as well as sustained release formulations, controlled release formulations, targeting formulations, and various micro-particular administration systems.

Various vehicles well known in the art may be widely used so as to formulate the unit dosage form into tablets. Exemplary vehicles are, for example, diluents and absorbants, such as starch, dextrin, calcium sulfate, lactose, mannitol, sucrose, sodium chloride, glucose, urea, calcium carbonate, bolus alba, microcrystalline cellulose, aluminum silicate, and the like; moisturizing agents and binding agents, such as water, glycerol, polyethylene glycol, ethanol, propanol, starch slurry, dextrin, syrup, honey, glucose solution, gum arabic slurry, gelatin slurry, sodium carboxymethyl cellulose, shellac, methyl cellulose, potassium phosphate, polyvinylpyrrolidone, and the like; disintegrants, such as dried starch, alginate, agar, phaeophytal starch, sodium bicarbonate and citric acid, calcium carbonate, polyoxyethylene sorbitan fatty acid ester, sodium lauryl sulfonate, methyl cellulose, ethyl cellulose, and the like; disintegration inhibiting agents, such as sucrose, glycerol tristearate, cacao butter, hydrogenated oil, and the like; absorption promoting agents, such as quarternary ammonium salt, sodium dodecyl sulfate, and the like; lubricants, such as talc, silicon dioxide, corn starch, stearate, boric acid, liquid paraffin, polyethylene glycol, and the like. The tablets may be further formulated as coated tablets, such as sugar-coated tablets, film-coated tablets, enteric coated tablets, or bilayer tablets and multilayer tablets.

In order to formulate the unit dosage form into pills, for example, various vehicles well known in the art may be widely used. Examples of vehicles are, for example, diluents and absorbents, such as glucose, lactose, starch, cacao butter, hydrogenated vegetable oil, polyvinylpyrrolidone, kaoline, talc, and the like; adhesives, such as arabic gum, tragacanth gum, gelatin, ethanol, honey, liquid sugar, rice paste or panada; disintegrants, such as agar, dried starch, alginate, sodium lauryl sulfonate, methyl cellulose, ethyl cellulose, and the like.

In order to formulate the unit dosage form into capsules, the compound of the present invention as active ingredients is mixed with various vehicles described above, the resulting mixture is placed into hard gelatin capsules or soft capsules. The compound of the present invention as active ingredient may also be formulated into microcapsules, mixed with aqueous media to form into suspensions, filled into hard capsules or formulated into injections for use.

For example, the compound of the present invention may be formulated into formulations for injection, such as solution, suspension, emulsion, lyophilized powder for injection, which may be aqueous or non-aqueous, may comprise one and/or more pharmaceutically acceptable vehicles, diluents, binding agents, lubricants, preservatives, surfactants, or dispersants. Diluents may be selected, for example, from water, ethanol, polyethylene glycol, 1,3-propylene glycol, ethyoxylated isostearyl alcohol, polyoxylated isostearyl alcohol, polyoxyethylene sorbitan fatty acid ester, and the like. Furthermore, appropriate amount of sodium chloride, glucose or glycerol may be added into the formulations for injection in order to prepare isotonic injections. Conventional solubilizing agents, buffering agents, and pH adjusting agents may also be added. These are commonly used in the art.

In addition, coloring agents, preservatives, flavors, flavoring agents, sweetening agents, or the like may be added to the pharmaceutical formulations if desired.

In order to fulfill the administration and increase the therapeutic effects, the medicaments or the pharmaceutical composition of the present invention may be administered via any administration route well known in the art.

The administration dose of the compound of the present invention or the pharmaceutical composition comprising the same depends on many factors, for example, the nature or severity of the disease to be prevented or treated, sex, age, body weight, personality and individual response of the patient or the animal, the route of administration, the frequency of administration and the therapeutic purpose. Therefore, the therapeutic dose in the present invention may vary in a wide range. Generally, the dose of the pharmaceutical ingredients in the present invention is well known to those skilled in the art, and may be suitably adjusted depending on the exact amount of the compound of the present invention contained in the final formulation of the composition, in order to reach a therapeutically effective dose, and thus to accomplish the preventive or therapeutic purpose of the present invention. Suitable daily dose of the compound of the present invention preferably lies in the range from 0.1 to 100 mg/kg body weight, more preferably from 0.1 to 100 mg/day/person. The dosage may be in a single dosage form or divided into more than one, for example 2, 3, or 4 dosage forms for administration, depending on clinical experiences of physicians, and also includes other dosage regimes using other therapeutic means.

The total dosage needed in each therapy may be administered in more than one dose, or just in one dose. The compound or the composition of the present invention may be administered alone, or in combination with other therapeutic agents or allopathic agents with necessary adjustment to the dosage.

Terms:
L-NBP: L-n-butylphthalide
2-VO model: permanent ligation of bilateral common carotid arteries

BRIEF DESCRIPTION OF DRAWINGS

FIG. 2A showed changes of latencies during training; FIG. 2B showed the results in platform exploration tests after the removal of the platform. The results were measured as the detention time of rats in the quadrant (Q4) where the platform was positioned, when rats were allowed to swim freely for 60 seconds. Each value was expressed as mean±standard error. 12-14 rats were included in each group. # $p<0.05$, as compared with those of the sham surgery group (sham). * $p<0.05$ as compared with those of the vehicle control group (vehicle).

FIG. 6(A-B). Effects of L-NBP on impaired memory induced by continuous perfusion of Aβ (1-40) into lateral ventricles in rats. Working memory tests (5 times each day) were performed on the 14-16$^{th}$ day after perfusion of Aβ (1-40). FIG. 6A showed changes of latencies during the first test; FIG. 6B showed changes of latencies during the subsequent 4 tests. Each value was expressed as mean±standard error. 10 rats were included in each group. # # $p<0.01$ as compared with those of the sham surgery group (sham). * $p<0.05$ as compared with those of Aβ (1-40) model group (vehicle).

DETAILED DESCRIPTION OF THE INVENTION

1. EXAMPLE 1

Therapeutic Effects of L-NBP on Vascular Dementia, One of Senile Dementias

Materials and Methods
Reagents and Chemicals
L-, D-, DL-NBP were synthesized in house, with optical and chemical purity of >98%. Optical rotations were −66.49, +66.88, and 0 degree respectively. They were formulated in vegetable oil.
Equipments
Morris' Water Maze Automatic Monitor, Step-through apparatus were developed by the instrumental and electronic lab of the Institute of Materia Medica, Chinese Academy of Medical Sciences.
Preparation of 2-VO Model
Male Wistar rats, which were 10-weeks old and weighed approximately 280 grams, were used. 5 animals were placed in each cage, while the room temperature was kept at 23° C., with food and water freely accessible. Rats were anaesthetized with sodium pentobarbital (40 mg/kg), then bilateral common carotid arteries were exposed and the envelope of common carotid arteries and vagus nerve was carefully separated. For the hypoperfusion model group, bilateral common carotid arteries were ligated with 5-0 silk thread. For the sham surgery group, the same operation was conducted but with no ligation of bilateral common carotid arteries. A little of sterile crystalline sulfanilamide powder was applied on the wound after the surgery, then the skin was sutured. One month after the surgery, water maze and step-through test were performed.
Experimental Grouping and Design
Rats were randomly assigned into 8 groups, with 10 animals per group. 1) sham surgery group: the same operation as that in hypoperfusion group was conducted but without ligation of bilateral common carotid arteries; 2) solvent control group: only vegetable oil was orally administered; 3) DL-NBP 10 mg/kg group; 4) DL-NBP 30 mg/kg group; 5) L-NBP 10 mg/kg group; 6) L-NBP 30 mg/kg group; 7) D-NBP 30 mg/kg group; Respective medicines or solvent were drenched since the 10th day after the surgery. Water maze experiments were performed on the 29-33rd days since the surgery, while step-through tests were performed on the 34-35th days since the surgery. Animals were killed for biochemical assay or pathological examination on the 36th day. In all the ethological tests, medicines were administered 40 minutes prior to respective test.

Water Maze Experiment

Morris' water maze is mainly composed of a metal cylindral water tank (with a height of 60 cm, and a diameter of 120 cm) and an automatic apparatus for displaying, monitoring and recording, and safety island (a platform with a diameter of 10 cm). Clear water was previously added into the tank, then 1000 g of fresh milk powder in water was added in order to make the tank opaque and a water level of 15 mm above the platform. As a result, animals could not reach the platform acoustically, visually or olfactorily, thus determining the sensitivity of animals to spatial orientation. The water temperature was kept at 23±1° C., and the tank was divided into four quadrants (east, south, west and north) with the platform being positioned in the center of the south-western quadrant. The swimming activity of each rat was monitored through a television set directly connected to a computer for analysis. The water maze experiments were performed for five consecutive days. Each rat was trained twice daily for searching for the platform, beginning from the center of north-eastern quadrant or north-western quadrant respectively, with the head toward the tank wall when entering into water. The interval between the 2 trainings was 10 minutes. The time required for finding the platform (latency) was recorded and the results of the 2 tests were averaged. If a rat did not find the platform within 60 seconds, the latency of the rat was designated as 60 seconds. No matter whether or not the rats found the platform within 60 seconds, each rat was kept on the platform for 10 seconds. Prior to the first test, each rat was placed on the platform for 10 seconds for adaptation. As the number of the training increased, the latencies to find the safety island in each group were reduced. After the last training, an exploration experiment was conducted. The platform was removed and the rats were allowed to swim freely to search for the platform for 60 seconds. The time spent in each quadrant was recorded. It was shown that the time the rats kept in the original quadrant where the platform was positioned was longer, indicating that the rats had established a memory of the target space.

Their search strategies could be classified into 4 types: (1) peripheral. Rats moved along the peripheral wall of the tank without search motivation; (2) random. Rats searched without clear direction; (3) purposive, the rats had memorized the location of the platform but without certainty, and turned around less than 4 times before finding out the safety island; (4) linear, the rats had memorized the location of the platform with certainty, and swam directly towards the safety island. The results were expressed as the time the rats spent to find the safety island, i.e. latency, and their search strategies. Detection of Choline Acetyltransferase, Anti-oxidative Enzyme and MDA Rats were decapitated to remove brains, the cortex and hippocampa tissues were isolated in ice bath and weighed, then immediately kept in liquid nitrogen for later use. The resulting sample was added to 0.05 mol/l of precooled potassium phosphate buffer, pH 7.0 (containing 0.5 mol/l of EDTA and 7% of glycerol), and then homogenized into 10% of homogenate. The levels of proteins were determined quantitatively by Lowry colorimetric assay.

1. Determination of choline acetyltransferase (ChAT): Into the reaction were added 40 µl each of 0.5 mol/l sodium phosphate buffer, 0.0062 mol/l acetyl CoA, 1.0 mol/l choline chloride, 76 µmol/l neostigmine methylsulphate, 3 mol/l NaCl and 0.011 mol/l EDTA, 0.5 mol/l creatinine hydrochloride, and finally distilled water was added into each tube until 0.8 ml of total volume was reached. After incubating at 37° C. for 5 minutes, 200 µl of the homogenate was added into each tube. Then each tube was kept in boiling water bath for 2 minutes, and 0.8 ml of 2.5 mmol/l sodium arsenate was added. The mixtures were centrifuged at 15000×g for 3 minutes at room temperature, and 2.0 ml of the resulting supernatant was added into 40 µl of 3 mmol/l 4-PDS. After the reactions were incubated at 25° C. for 15 minutes, optical densities were determined ($\delta$=324 nm). ChAT activities were accordingly calculated and expressed in nmol CoA·SH/mg protein/hr.

2. Superoxide dismutase (SOD) and malondialdehyde (MDA) were assayed according to the instructions contained in the kit provided by Nanjing Jiancheng Biotech Inc.

Pathological and Immunohistochemical Detection 4-6 animals were chosen from each group randomly. After the ethological experiments, rats were anaesthetized with pentobarbital (100 mg/kg ip). Animal's skin and thorax was sequentially cut open and the heart was sufficiently exposed. Left tip of the heart was cut open, a perfusion needle was inserted along the aorta. After clamping with hemostat, physiological saline was infused. Right atrium was cut open at the lower portion, then physiological saline was infused for 15-20 minutes (200-300 ml). After the effluent became clear, 4% paraformaldehyde in PBS was infused instead for another 15-20 minutes (150-200 ml), until the animal became stiff and the liver became white. Then the brain was obtained by decapitation, and after anterior telencephalon and posterior cerebellum were excised, fixed in 4% paraformaldehyde for another 48 h (paraffin section) or in 20% sugar-paraformaldehyde solution for 48 h (cryosection).

After being fixed, embedded and sectioned, paraffin sections were Hematoxylin-Eosin (HE) stained and K-B (Kluver-Barrera Luxol fast blue) stained for pathological examination, and assayed by immunohistochemical methods to determine the change of the level of GFAP in brain tissues.

Statistical Analysis

All results were expressed as mean±standard error. Comparison of latencies between groups in water maze experiment was performed using two-factor analysis of variance. Difference between groups was determined using post hoc LSD or Turkey test. Platform exploration test in water maze experiment was analyzed using one-factor analysis of variance. Step-through experiment was analyzed using Kruskal-Wallis test and Mann-Whitney U test. Biochemical assays were analyzed using one-factor analysis of variance. A difference was considered significant when p<0.05.

Results

Effect of L-NBP on the Learning and Memory of Rats in Water Maze Experiment

In the water maze experiment, learning and detention tests are often employed to assess stereotaxic memory of hypoperfused rats. On the first day of training, no significant difference was observed among the groups. After training for 5 days, the search strategy of the sham surgery group changed from peripheral and random to purposive and linear, and the latency (12.6±3.34 seconds) reduced significantly. However, the search strategy of the solvent control group did not change evidently and was still peripheral and random, the latency (47.6±5.88 seconds) being not greatly reduced. The difference between the two groups was significant (p<0.01). The search strategy of L-NBP 10 mg/kg group changed from peripheral and random to purposive and linear, and the latency (26.85±5.98 seconds) was reduced obviously. The difference was significant as compared with the solvent control group (p<0.001, two-factor analysis of variance), but not significant as compared with the sham surgery group. Other agents such as DL-NBP 10 mg/kg, DL-NBP 30 mg/kg and D-NBP 30 mg/kg showed no obvious improved effect (see FIGS. 1A, B and 2). After the learning and training period of 5 days, the platform exploration experiment was conducted. The safety island was removed to determine whether the rats had established stereotaxic memory of the safety island. Except for the solvent control group, the detention time of all rats in the target quadrant was more than 25%, demonstrating that all of them had established stereotaxic memory of the safety island. The detention time of the sham surgery group (17.73±1.19 seconds) was evidently longer than that of the solvent control group (14.40±0.73 seconds), representing significant difference as determined by one-factor analysis of variance (p<0.05, see FIG. 3). The detention time of L-NBP 10 mg/kg group at the target quadrant (17.62±1.27 seconds, p<0.05) was significantly longer than that of the solvent control group, while the DL-NBP groups (10 mg/kg and 30 mg/kg) showed no effect. No difference existed between the swimming speeds of the groups, thus eliminating the variation derived from animal mobilities. The results above indicated that only L-n-butylphthalide could significantly ameliorate impaired short-term memory and spatial orientation of rats with poor blood supply to brain, but racemic (DL-) and D-n-butylphthalide could not.

Effects on SOD, ChAT Activity and MDA Content

SOD is one of the important anti-oxidative enzymes. In the normal control group, SOD activity is 100.07±3.64 (NU/mg protein) in cortical tissues, and 57.90±7.41 (U/mg protein) in hippocampal tissue. After permanent ligation of bilateral common carotid arteries in rats, the SOD activity in hippocampus increased significantly compared with that of the control group (p<0.05). Probably this was a compensatory response. After treatment of L-NBP (10 mg/kg), the SOD activity evidently returned close to the normal level (p<0.05). MDA is a marker of lipid peroxidation, and could indicate the level of lipid peroxidation in vivo and indirectly indicate the degree of cell damage. In the experiment, the content of MDA in the cortex of the model group increased 19.9%, being significantly different from that in the normal control group (p<0.001). After treatment with L-NBP (10 mg/kg), the content of MDA in cortex significantly reduced 20.7% (p<0.001). After permanent ligation of bilateral common carotid arteries, the cortical ChAT activity significantly reduced 34.4% as compared with that of the normal control group (p<0.05), suggesting that hypoperfusion could induce damages to cholinergic neural function. Comparatively, after continuous administration of L-NBP (10 mg/kg) for 16 days, the cortical CHAT activity could be improved 37.1% as compared with that of the model group, showing significant difference (p<0.05). (see Table 1).

TABLE 1

Effects of L-NBP on the cortical and hippocampal SOD activities and MDA contents in hypoperfused rats (n = 7-9)

| group | SOD activity (NU/mg protein) | | MDA content (nmol/mg protein) | | ChAT activity (% of sham) | |
|---|---|---|---|---|---|---|
| brain region | cortex | hippocampus | cortex | hippocampus | cortex | hippocampus |
| sham surgery | 100.07 ± 3.64 | 57.90 ± 7.41 | 3.13 ± 0.10 | 3.03 ± 0.12 | 100.0 ± 13.3 | 100.0 ± 7.2 |
| solvent control | 114.42 ± 7.82 | 81.16 ± 6.84* | 3.91 ± 0.22*** | 3.63 ± 0.45 | 65.6 ± 15.1* | 102.6 ± 15.1 |
| L-NBP (10 mg/kg) | 98.84 ± 5.53 | 57.60 ± 3.86* | 3.10 ± 0.09*** | 3.42 ± 0.12 | 104.3 ± 8.2* | 110.0 ± 13.5 | p < 0.05,
p < 0.001 as compared with the sham surgery group;
*p < 0.05,
***p < 0.001 as compared with the solvent control group.

Pathological and Histochemical Effects

After permanent ligation of bilateral common carotid arteries, the number of neurons in the cortical and hippocampal regions was significantly reduced in the model group, cells wrinkled and neurons were strongly stained. Comparatively, neural damage induced by hypoperfusion could be significantly ameliorated by L-NBP (10 mg/kg) treatment. It was reported in literature that bilateral common carotid artery ligation could induce the activation of glial cells in brain, accompanied with sparse substantia alba. The sparsity of the substantia alba can generally be classified into 4 grades according to the severity: grade 0, normal; grade 1, misarrangement of nerve fibres; grade 2, evident formation of vacuola; grade 3, disappearance of fibres with myelin sheath. In our experiment, compared with the normal control group, optic tracts of the model group presented evidently sparse substantia alba and a number of vacuola appeared. Extended administration of L-NBP (10 mg/kg) could significantly ameliorate the condition, resulting in significant reduction of vacuola in optic tracts. It was shown in immunohistochemical experiments that GFAP-positive astrocytes were rarely detected in regions such as hippocampus, caudate nucleus, and corpus callosum in the normal control group, but after bilateral ligation of common carotid arteries for 4 weeks, plenty of GFAP-positive astrocytes and microglial cell appeared. After L-NBP (10 mg/kg) treatment, the number of GFAP-positive astrocytes greatly reduced (see FIGS. 3, 4).
Conclusion From the results above, it can be concluded that 10 mg/kg L-NBP could significantly ameliorate disorders in short-term memory and spatial orientation in 2-VO animals, while neither racemic butylphthalide nor D-butylphthalide were effective to ameliorate impaired memory function. In the study, the administration began on the $10^{th}$ day after 2-VO (and until the $35^{th}$ day) to investigate therapeutic effect of drugs on degenerative changes of neurons induced by hypoperfusion and thus to eliminate the influence on acute hypoperfusion ischemia period.

L-NBP could improve ChAT activity, indicating that L-NBP could increase ACh level of cholinergic neurons and thus could contribute to improve memory. In addition, L-NBP could significantly inhibit oxidative damages, suggesting that L-NBP could reduce damages to neural cells. Cerebral hypoperfusion induced by 2-VO was characterized in sparse substantia alba, and increased vacuola and glial cells (Narri. et al. Chronic cerebral hypoperfusion-induced neuropathological changes in rats. Jpn. J. Psychopharmacol. 1998; 18:181-188), while L-NBP could improve all these pathological changes. The action mechanism above presented the evidence that L-NBP could ameliorate impaired memory induced by 2-VO in rats. The above results suggested the possibility of using L-NBP to treat or prevent vascular dementia effectively.

EXAMPLE 2

L-NBP Could Significantly Ameliorate Symptoms of Senile Dementia Induced by Amyloid-β (1-40)

Materials and Methods
Reagents and Chemicals

L-NBP was synthesized in house and was formulated into vegetable oil. Aβ (1-40) was purchased from Sigma. Alzet brain micro-osmotic pump perfusion apparatus was purchased from DURECT, U.S.
Equipments For Morris' Water Maze Automatic Monitor and experimental protocols, reference may be made to the experiments of learning and memory damage of rats induced by brain hypoperfusion.
Model Preparation Male Wistar rats, which were 10-weeks old and weighed approximately 280 grams, were used. One animal was placed in one cage, while the room temperature was kept at 23° C., with food and water freely accessible. Rats were anaesthetized with sodium pentobarbital (40 mg/kg), and were fixed to stereotaxic apparatus with the position of ventral decubitus. Head skin was cut open, a cannula for Aβ (1-40) perfusion was implanted into right ventricle. According to the stereotaxic profile of rat brain by Paxions and Watson, the implantation site was located 0.3 mm behind and 1.1 mm in the right side of anterior fontanelle, with the depth of 4.0 mm. The cannula was connected to a micro-osmotic pump. The pump was placed on the back of the rat. Aβ (1-40) was dissolved in 35% acetonitrile/0.1% trifluroacetic acid, and was continuously perfused intracerebroventricularly (i.c.v.) at 300 pmol/day, while only the solvent (35% acetonitrile/0.1% trifluroacetic acid) was perfused in the control group. Previous experiments had demonstrated that the solvent at this flow rate would not induce behavioral and neurochemical changes in rats.

Experimental Grouping and Design

Rats were randomly classified into 8 groups, with 10 animals per group. 1) the sham surgery group: only 35% acetonitrile/0.1% trifluroacetic acid+solvent was perfused into the ventricles of the rats; 2) the model group: Aβ (1-40)+solvent; 3) Aβ (1-40)+L-NBP 10 mg/kg group; 4) Aβ (1-40)+L-NBP 30 mg/kg group. Respective drug or solvent was drenched since the $2^{nd}$ day after the surgery. The water maze experiment was performed on the 9-13 day after the surgery, while the platform exploration experiment was performed on the $13^{th}$ day, and the working memory test was performed on the $14$-$16^{th}$ days. Animals were decapitated to remove brains for biochemical assay on the $17^{th}$ day. In all ethological tests, medicines were administered 40 minutes prior to the respective test.

Water Maze Experiment

The water maze training experiment was performed on the $9$-$13^{th}$ day after icv Aβ (1-40), and the platform exploration experiment was performed on the 13 day after that. The working memory test was performed on the $14$-$16^{th}$ day after icv Aβ (1-40) (see the figure above), which investigated the ability of rapid learning and spatial memory in animals when the platform and quadrant were changed, based on the fact that animals had memorized in some extent after training and platform exploration experiment. Experimental procedure was similar to the standard water maze training experiment except that the platform's location was changed every day. The experiment was conducted five times every day, allowing the rats to start swimming from five water-entry sites respectively. The first experiment on each day was referred as the demonstration experiment, in which the rats were allowed to swim to the platform at a new location and to stay for 10 seconds. In the following 4 experiments, the location of the platform was kept constant, yet the water entry sites were within different quadrants. The latency of working memory was calculated by averaging those of the $2$-$5^{th}$ experiments, and the ability of working memory of each rat was calculated by averaging the experimental values in 3 days.
Biochemical Assay Malondialdehyde (MDA) and glutathione peroxidase (GSH-Px) were determined by the same assays as above.
Statistical Analysis All results were expressed in mean±standard error. Comparison of latencies between groups in water maze experiment was performed using two-factor analysis of variance in replicate. Comparison between groups was performed using post hoc LSD or Turkey test. Platform exploration test in water maze experiment, working memory test and biochemical assay were analyzed using one-factor analysis of variance. A difference was considered significant when $p<0.05$.

Results
Effect of L-NBP on Learning and Memory of Rats in Water Maze Experiment

Figure 5:
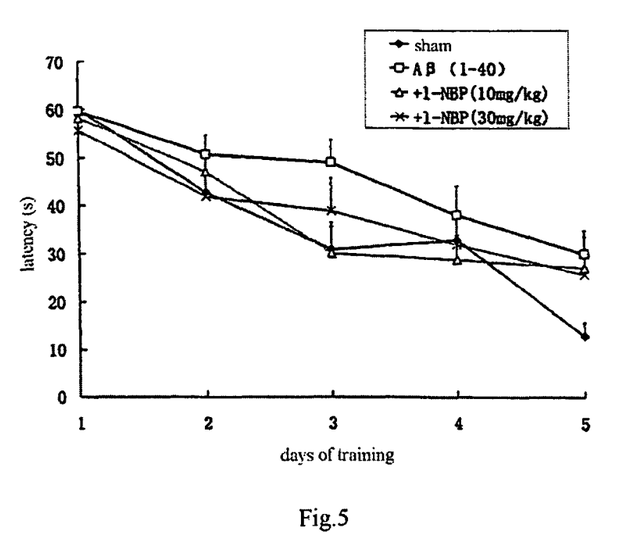
FIG. 5. Effects of L-NBP on impaired memory in water maze experiments after continuous perfusion of Aβ (1-40) into lateral ventricles in rats. Changes of latencies of escape during training were shown. Each value was expressed as mean±standard error. 10 rats were included in each group.

On the first day of training, no significant difference was present among the groups. After being trained for 5 days, the search strategy of the rats in the sham surgery group changed from peripheral and random to purposive and linear, and the latency (13.02+2.77 seconds) was reduced significantly. However, the search strategy of the rats in the model group did not change evidently and was still peripheral and random, the latency (30.182.77 seconds) was reduced significantly. However, the search strategy of the rats in the model group did not change evidently and was still peripheral and random, the latency (30.18+4.81 seconds) not being reduced obviously. The difference between these two groups was significant ($p<0.01$). After L-NBP treatment, the latencies of the rats in the water maze experiment were reduced greatly. The search strategy of the rats in the L-NBP 10mg/kg and 30mg/kg groups changed from peripheral and random to purposive and linear, and the latencies were 27.28+6.42 or 25.88+5.51 seconds respectively, so the difference was significant as compared with the model group ($p<0.05$, two-factor analysis of variance), while no significant difference was present as compared with the sham surgery group. It suggested that rats after L-NBP treatment had returned nearly to normal level (see Figure 5). In the working memory test, latencies in the 1$^{st}$ and 2-5$^{th}$ experiments were shown in Figures 6A and 6B, respectively. No significant difference was present among the latencies of various groups in the first demonstration experiment. But in the following 4 experiments, the latencies of the sham surgery group and of the model group were 9.15+0.91 seconds and 14.05+1.88 seconds, respectively. The latter was evidently prolonged and the difference was significant ($p<0.01$). Therefore, L-NBP could improve the working memory of rats in a dose-dependent manner ($p<0.01$).

L-NBP Could Increase the Activity of GSH-Px and Reduce the Content of MDA.

GSH-Px is an important anti-oxidative enzymes. In our experiments, the cortical GSH-Px activity of the sham surgery group was 15.86±0.91 (U/mg protein); while the hippocampal GSH-Px activity was 16.19±1.19 (U/mg protein). After continuous perfusion of Aβ (1-40), the cortical and hippocampal GSH-Px activities in the rats reduced 29.5% and 42.4% respectively, as compared with that of the sham surgery group. There was significant different therebetween ($p<0.01$ and $p<0.001$). After L-NBP treatment, the GSH-Px activity of the 30 mg/kg L-NBP group increased significantly ($p<0.01$), while 10 mg/kg L-NBP could also increase GSH-Px activity but of no statistically significant difference. MDA is a marker of lipid peroxidation, indicating the degree of lipid peroxidation in vivo, and indirectly indicating the degree of cell damages. In the present experiment, after continuous perfusion of Aβ (1-40), the cortical and hippocampal MDA contents increased 25.7% and 23.6% respectively, being significantly different from those of the sham surgery group ($p<0.05$ and $P<0.01$). After L-NBP treatment, the cortical and hippocampal MDA content significantly reduced 28.4% and 24.3% respectively in the 10 mg/kg group ($p<0.05$ and $p<0.01$). The effects in the 30 mg/kg group were weaker than that in the 10 mg/kg group, yet were still significantly different from that in the Aβ (1-40) model group ($p<0.05$). The results were shown in Table 2.

TABLE 2

Effects of L-NBP on the cortical and hippocampal SOD activities and MDA contents after continuous perfusion of Aβ (1-40) (n = 7)

| group | GSH-PX (U/mg protein) | | MDA (nmol/mg protein) | |
|---|---|---|---|---|
| | cortex | hippocampus | cortex | hippocampus |
| sham surgery | 15.86 ± 0.91 | 16.19 ± 1.19 | 1.10 ± 0.09 | 1.13 ± 0.06 |
| model Aβ (1-40) | 11.18 ± 1.32$^{\#\#}$ | 9.32 ± 1.01$^{\#\#\#}$ | 1.48 ± 0.14$^{\#}$ | 1.48 ± 0.12$^{\#\#}$ |
| L-NBP (10 mg/kg) | 11.73 ± 0.53 | 12.73 ± 1.34 | 1.06 ± 0.05* | 1.12 ± 0.07** |
| L-NBP (30 mg/kg) | 15.40 ± 1.03** | 18.91 ± 1.16** | 1.06 ± 0.10* | 1.15 ± 0.07* |

$^{\#}p < 0.05$,
$^{\#\#}p < 0.01$,
$^{\#\#\#}p < 0.001$ as compared with the sham surgery group;
$*p < 0.05$,
$**p < 0.01$ as compared with the model group.

Discussion

Impaired memory induced by continuous perfusion of Aβ (1-40) into rats was a well-established model to investigate the effect of medicines on AD treatment. According to the results above, L-NBP had evident effects on the model of vascular dementia induced by 2-VO ischemia, but also can significantly ameliorate impaired short-term memory and stereotaxic memory induced by continuous perfusion of Aβ (1-40) into lateral ventricle in rats. It suggested that L-NBP could significantly ameliorate impaired short-term memory and stereotaxic memory induced by various causes. Furthermore, L-NBP could prevent oxidative damages (increasing the GSH-Px activity and reducing the MDA content). This effect, in combination with L-NBP's evident brain-protecting effect, suggested L-NBP could treat and prevent senile dementia.

The invention claimed is:
1. A method for treating dementia, comprising administering a therapeutically effective amount of the isolated optical isomer of L-n-butylphthalide represented in formula (I) to a patient

(I)

thereby treating dementia.

2. The method according to claim 1, wherein the dementia is treated in a patient having Alzheimer's disease.

3. The method according to claim 1, wherein the dementia is vascular dementia.

4. The method according to claim 1, wherein the therapeutically effective amount is in the range of 0.1-100 mg/kg/day.

5. The method according to claim 1, wherein the isolated optical isomer of L-n-butylphthalide is present in a pharmaceutical composition substantially free of D-n-butylphthalide.

6. The method according to claim 5, wherein the pharmaceutical composition is in the form of tablets, capsules, pills, injections, sustained release formulation, controlled-release formulation or various microparticular delivery systems.

\* \* \* \* \*

UNITED STATES PATENT AND TRADEMARK OFFICE
CERTIFICATE OF CORRECTION

PATENT NO. : 8,552,058 B2  
APPLICATION NO. : 11/629964  
DATED : October 8, 2013  
INVENTOR(S) : Yipu Fang et al.

It is certified that error appears in the above-identified patent and that said Letters Patent is hereby corrected as shown below:

Title Page, Assignee should read:

--(73) Assignee: CSPC Zhongqi Pharmaceutical Technology (Shijazhuang) Co., Ltd. (Shijazhuang, Hebei, CN) INSTITUTE OF MATERIA MEDICA, CHINESE ACADEMY OF MEDICAL SCIENCES (BEIJING, CN)--

Signed and Sealed this  
Eleventh Day of March, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,552,058 B2  
APPLICATION NO. : 11/629964  
DATED : October 8, 2013  
INVENTOR(S) : Yipu Feng et al.

Page 1 of 1

It is certified that error appears in the above-identified patent and that said Letters Patent is hereby corrected as shown below:

Title Page, Assignee should read:

--(73) Assignee: CSPC Zhongqi Pharmaceutical Technology (Shijazhuang) Co., Ltd. (Shijazhuang, Hebei, CN)  
INSTITUTE OF MATERIA MEDICA, CHINESE ACADEMY OF MEDICAL SCIENCES (BEIJING, CN)--

This certificate supersedes the Certificate of Correction issued March 11, 2014.

Signed and Sealed this  
Ninth Day of June, 2015

Michelle K. Lee  
*Director of the United States Patent and Trademark Office*